United States Patent [19]

Mehr

[11] Patent Number: 4,854,690

[45] Date of Patent: Aug. 8, 1989

[54] EYE SIGHT RESTORER DEVICE AND METHOD

[76] Inventor: Fred E. Mehr, P.O. Box 1117, Hilo, Hi. 96721

[21] Appl. No.: 160,830

[22] Filed: Feb. 26, 1988

[51] Int. Cl.[4] ........................... A61B 3/10; A61F 5/08

[52] U.S. Cl. .................................... 351/203; 351/221; 351/158; 128/76.5

[58] Field of Search ................. 351/41, 156, 158, 203, 351/246, 221; 362/103; 128/76.5

[56] References Cited

U.S. PATENT DOCUMENTS

| | | | |
|---|---|---|---|
| 2,190,564 | 2/1940 | Jones | 351/203 |
| 4,057,054 | 11/1977 | Giannone | 351/158 |
| 4,396,259 | 8/1983 | Miller | 351/158 |
| 4,541,696 | 9/1985 | Winger | 351/156 |
| 4,657,364 | 4/1987 | Murrell | 351/156 |

*Primary Examiner*—Rodney B. Bovernick
*Attorney, Agent, or Firm*—Antonelli, Terry & Wands

[57] ABSTRACT

A device and method for relieving eye strain which uses a head band and light which is switched on and off when the user's eyelids are shut. The user controls the frequency with which the light is turned on and off by means of a hand-held battery pack and switch. On-and-off switching is continued in the absence of ambient light until the user feels sufficient relief.

6 Claims, 2 Drawing Sheets

EYE SIGHT RESTORER DEVICE AND METHOD

BACKGROUND OF MY INVENTION

The present invention relates to a method and device which relieve eye strain and, more particularly, to a method and device which can be in the form of an adjustable head band with a light switchable on and off to provide a rest effect for the wearer's eyes.

It has long been known that eye strain is caused by prolonged use of the eyes without proper exercise to lessen that strain. These finings date back to 1851 based upon the work of the German scientist Hermann von Helmholtz and were subsequently substantiated by the work of Dr. William Bates in the early twentieth century and more recently in 1983 in the published work of Dr. Marilyn Berret. Dr. Berret describes a "palming method" whereby a person uses the palms of the hands to cover the eyes and then expose them to light by removing the palms. I have found it is very difficult to stay relaxed for more than a few minutes when using her method, and she believes relaxation is an important part of the method.

Sight training and eye strain relieving techniques of several types have been known for some time. For instance, U.S. Pat. No. 2,690,173, shows the use of a headband device for exercising the eyes by means of regulated pressure to strengthen and adjust eyesight. However, this technique requires physical contact with the eyelids to achieve eyesight strengthening, and some persons may object to such physical contact.

U.S. Pat. No. 3,603,305 discloses an optical frame in which light bulbs are placed to obtain occlusion of the field of vision by recurrently flashing light against the inner surface of an occluded eyepiece so that light is reflected from that surface into the eye of the wearer to diminish his or her ability to perceive the field of vision with that eye. The intensity of the flashing light can be adjusted or varied. This device is not concerned with restoration of eyesight by the relaxation of strain and does not utilize a convenient headband. Rather, it is intended to fuse optical images from the fields of vision in a real world situation during treatment.

The eye relaxation method shown in U.S. Pat. No. 3,843,240 uses a blurry blob of green colored light which flickers at low frequency. It appear that this apparatus is intended to be used with the eyelids open, and thus it does not provide the needed eye relaxation to relieve strain and restore eyesight.

U.S. Pat. No. 2,057,983 describes an optical instrument that produces eye stimulation by using a filter appropriate to a patient's biotype. The filter absorbs or transmits light frequencies best adapted to stimulate or depress the nerve centers. The lamp is flashed on and off rhythmically at a desired speed. This flashing is repeated at intervals to recondition and correct abnormal visual problems. This instrument is not intended to be worn by the patient or used with the eyes closed during flashing of the light. U.S. Pat. No. 2,089,863 shows another form of exercise apparatus in which the eye muscles are treated by periodically flashing lights into open eyes.

The foregoing are merely illustrative of known techniques for eye stimulation and fusion training. Other examples are shown in U.S. Pat. Nos. 2,152,050; 2,899,956; 3,152,594; and 3,545,847.

I have recognized that the known techniques and apparatuses are either too complex or do not really correct eye strain on a long term basis. They are often uncomfortable to the user, such as the techniques which require some contact in the eye area or flash light into an open eye so as to cause discomfort.

SUMMARY OF MY INVENTION

It is the object of my invention to overcome the problems and disadvantages encountered with prior devices and methods for relieving eye strain or restoring sight to full vision with most subnormal functions.

It is a further object of my invention to provide a simple method and relatively uncomplicated apparatus to lessen eye strain and provide the needed rest for eyes which have been used on a prolonged basis without proper exercise.

I have achieved these objects by a method and device which utilizes light and dark contrasts in portable device carried on the head of the user such that the eyelids are kept in the strict position during operation of the device to provide maximum comfort to the wearer. The light is then flashed on and off such that the user first senses a light orange and red glow or cherry orange which can be flecked with green through the closed eyelids and then, when the light is shut off, perceives a fading dull green or grayish glow which eventually becomes black at which time the process is repeated.

BRIEF DESCRIPTION OF THE DRAWINGS

These and further features, objects and advantages of my invention will become more apparent from the following detailed description of a presently preferred embodiment when taken together with the accompanying drawing which shows, for illustrative purposes primarily, that embodiment and wherein.

DETAILED DESCRIPTION OF A PRESENTLY PREFERRED EMBODIMENT

Figure 1:
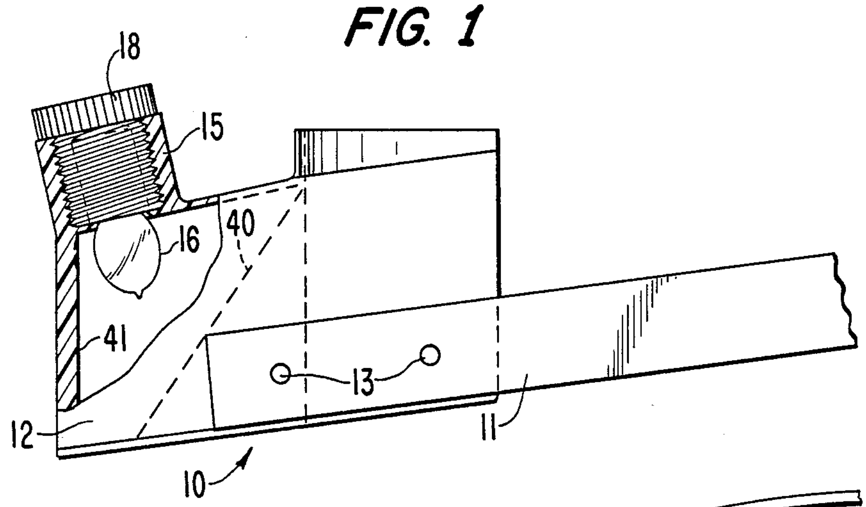
FIG. 1 is a side elevation of the front portion of a headband which utilizes my invention, with a front portion of the mechanism broken away to reveal details of the bulb and with the bulb socket housing in sectional view.
Figure 2:
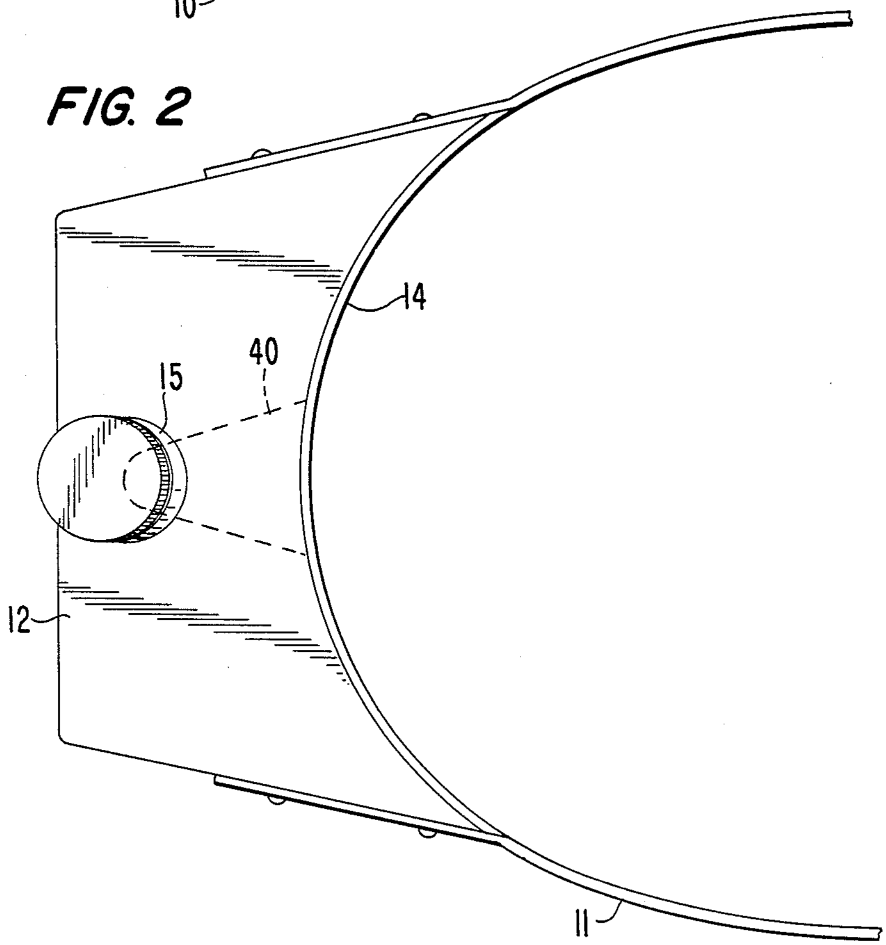
FIG. 2 is a top view of the headband front portion shown in FIG. 1.

Referring now to the drawings and, in particular, to FIG. 1, there is shown the eyesight strain relieving device designated generally by the numeral 10 for practicing my new and unique method to lessen eye strain and restore the normal use of the eyes. The device comprises an adjustable flexible headband 11, only a portion of which is shown, which can be adjusted to the size of any wearer's head by a buckle or clasp or other conventional adjusting means which is also not shown.

An eyesight restoring mechanism 12 is attached to the front of the headband 11 by rivets 13 or the like so that the mechanism 12 can be maintained in a fixed position relative to the wearer's head and eyes once the headband 11 is properly positioned and comfortable to the wearer. It is important that the mechanism keep out ambient room light and permit only the light from bulb hereinafter described to create the effect for relieving eye strain. The inside edge 14 of the mechanism 12 is contoured generally to the shape of a forehead and fitted with rubber or other soft material of sufficient thickness so that it generally matches the shape of a person's forehead and will thus be more comfortable to most people. A portion 40 is formed in the mechanism and can be fitted with rubber flexible enough so as to permit passage of the device over the nose and, when contacting the nose, to rest comfortably thereon.

The mechanism 12 forms, generally speaking, a parallelpiped body as viewed in FIG. 1 which has at the remote most end a protruding socket 15 for holding a bulb 16. For example, the bulb can be a standard 2.38 V, 500 MA flashlight bulb. The details of the bulb-and-socket arrangement are shown in more detail in FIGS. 3 to 5. The inside wall 41 of the mechanism 12 is covered with aluminum foil or other suitable reflecting material to provide maximum reflection of the light from the bulb for use in the method of my invention. The socket 15 can be formed integrally with the rest of the mechanism 12 which can be constructed from a suitable light weight, low cost plastic or other suitable material from the point of view of cost and weight. Alternatively, the mechanism 12 can be formed of composite materials so that the portion adjacent the wearer's forehead will adapt easily to the head shape.

Figure 3:
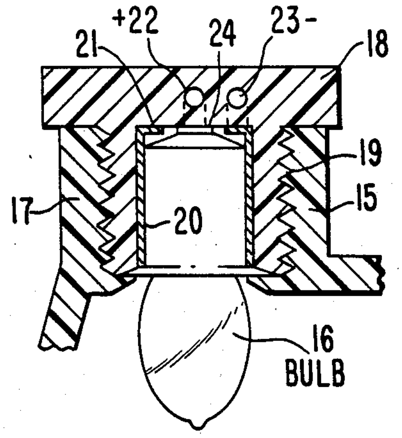
FIGS. 3, 4 and 5 are detailed side views of the bulb housing shown in FIG. 1.
Figure 4:
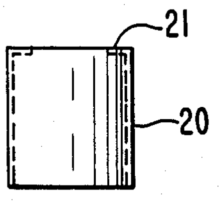
Figure 5:
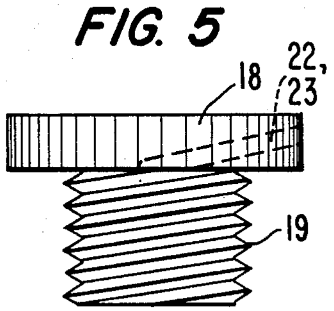

As shown in FIGS. 3 to 5, the socket 15 comprises a plastic housing 17 with internal threads and a plastic cap 18 with a hollow threaded depending portion 19 adapted to threadably engage securely in the housing 17 in a known manner. A cylindrical metal shell 20 having an annular wall 21 at one end snugly fits within portion 19 of the cap 18. Two holes 22, 23 are provided in the cap 18 for lead wires which connect with a metal contact 24 at the base of bulb 16 and the metal shell contact 20 at the annular wall 21 to form an electrical circuit which will allow selective switching on and off of the bulb. The details and operation of the bulb and electrical connections thereto are also conventional and need not be discussed in further detail.

Figure 6:
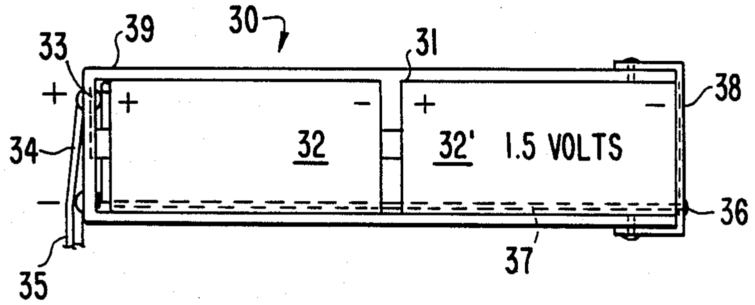
FIGS. 6, 7, and 8 are detailed side views of the battery and switch assembly case for switching the bulb on the headband selectively on and off.
Figure 7:
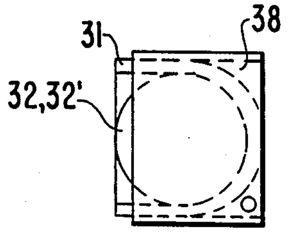
Figure 8:
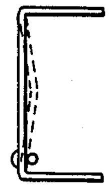

The wires passing through the passages 22, 23 in the cap 18 can be about 2 to 3 feet long and are connected to a battery case with a hand-operated switch designated by the numeral 30 in FIG. 6. Further details of the case 30 are shown in FIGS. 7 and 8. The case comprises a plastic housing 31 which accommodates two 1.5 volt "C" dry cell batteries 32, 32' connected in series. At one end of the housing 31, the positive terminal of battery 32 is adjacent a metal plate 33 which connects the batteries with one of the wires 34. The other wire 35 is connected to the housing 31 at end 36 of the plastic housing 31. A connection wire 37 permanently arranged in the housing 31 establishes a connection between wire 35 and the negative terminal of battery 32'. At the other end of the housing 31 is arranged a thin, flexible stainless steel finger switch 38 at which the connection wire 37 is attached by riveting or other known joining techniques. For example, the steel can be 0.0035 inch thick and is configured so that in the absence of finger pressure it is out of contact with battery 32' and provides an open circuit so that the bulb 16 is not switched on. In an alternative embodiment, the batteries 32, 32' can be normally biased away from contact with the positive terminal 33 by a spring 39 disposed between the battery 32 and the end wall of the housing 31. Upon pressing the switch with a finger to the position shown in dashed line in FIG. 8, the wearer of my invention can selectively turn the lamp 16 on and off by, respectively, establishing and breaking the circuit.

My invention is not limited to the foregoing embodiment. Two bulbs can be employed with similar results. I have found that periodic use of the apparatus has relieved pressure sore eyes and double vision. Although a user may perceive different light sensations with his or her eyes closed when the device is flashed, I have generally found that when the bulb is lighted so as to direct light through the closed lids, the user perceives spots of deep cherry orange color and flecks of light green through the pattern. The bulb is left on until the bulb has provided sufficient light to attain a similar color perception, then the bulb is switched off. With the lamp switched off, the sensation becomes light gray blended with pale green fading to gray and then totally black.

In operation, the user wears the device 10 upon his or her head when they feel the necessity to exercise their eyes and relieve eye strain. By operating the switch 38 with the fingers and the eye mask in place over the forehead, the user turns the lamps on until spots of deep cherry orange color are perceived then turns the lamp off until the user perceives the light gray turning to gray and finally black. At this point the switching on and off process is repeated until the user senses relief of eye strain. I have found, for example, that repetition of this process for about a half hour is sufficient, although it will vary from individual to individual.

While I have shown an described a presently preferred embodiment in accordance with my invention, it is to be understood that the same is susceptible of changes and modifications within the scope of my invention. Therefore, I do not intend to be limited to the details shown and described herein but intend to cover all such changes and modifications as are encountered by the scope of the appended claims.

I claim:

1. A device for relieving eye strain, comprising a light source adapted to be placed in proximity to and centrally of and to project light toward the closed eyes of a person who seeks eye strain relief, means for periodically switching said at least one light source on and off when the person's eyes are closed, including a low voltage portable direct current power supply, and means for retaining said light source on the head of the person and excluding ambient light from the closed eyes of the person.

2. A device according to claim 1, wherein said switching means includes a switch operable by the hand of the person at a periodic frequency determined by the person.

3. A device according to claim 1, wherein the retaining means is a adjustable head band.

4. A device according to claim 3, wherein the band consists of flexible material.

5. A device according to claim 1, wherein reflecting means are provided around a portion of said at least one light source for increasing the intensity of the light when switched on.

6. A method for relieving eye strain, comprising placing a light source in proximity to and centrally of and to project light toward the eyes of a person, while excluding ambient light from reaching the eyes;

closing the eyes;

switching from a low voltage portable direct current power supply said light source on and off periodically over a length of time sufficient to relieve the person's eye strain.

* * * * *